US00PP34979P2

(12) United States Plant Patent
Bacon et al.

(10) Patent No.: US PP34,979 P2
(45) Date of Patent: Feb. 14, 2023

(54) PEACH TREE NAMED 'SUPECH27'

(50) Latin Name: *Prunus persica*
Varietal Denomination: Supech27

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/882,333

(22) Filed: Aug. 5, 2022

Related U.S. Application Data

(60) Provisional application No. 63/285,235, filed on Dec. 2, 2021.

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
CPC ..... A01H 6/7463
See application file for complete search history.

*Primary Examiner* — Anne Marie Grunberg
(74) *Attorney, Agent, or Firm* — Knobbe, Martens, Olson & Bear, LLP

(57) ABSTRACT

The new variety of peach tree 'Supech27' is characterized by having mid-season ripening, very large-size fruit, with a dark red over-color and medium adherence of the stone to the flesh.

1 Drawing Sheet

Latin name of the genus and species claimed: *Prunus persica.*

Variety denomination: 'SUPECH27'.

BACKGROUND AND SUMMARY OF THE INVENTION

This invention relates to the discovery and asexual propagation of a new and distinct variety of peach, *Prunus persica* cv. 'Supech27'. The variety 'Supech27' was originated by hybridization and was first selected in July 2016 by Terry A. Bacon and Terrence J. Frett as breeder number: 'PE1942W'. The new variety was first evaluated by Terry A. Bacon and Terrence J. Frett near Wasco, Calif. in Kern County.

The seed parent is 'PE1192W' (unpatented breeding selection), and the pollen parent is bulk pollen of seven unpatented breeding program selections: 'PE1391W', 'PE1465W', 'PE1468WF', 'PE1503W', 'PE1505WF', 'PE1525W' and 'PE1541W'. The parent varieties were first crossed in March 2013, with the date of sowing being March 2014, and the date of first flowering being March 2016. The new peach variety 'Supech27' was first asexually propagated by Terry A. Bacon and Terrence J. Frett near Wasco, Kern County, Calif. in February 2017 by dormant grafting.

The new variety 'Supech27' is characterized by having very large-size fruit with a dark red over-color and white flesh. The fruit ripens mid-season, and has medium adherence of the stone to the flesh.

The new variety 'Supech27' resembles its seed parent 'PE1192W' in that both have fruit with white flesh, however the new variety is distinguished from its seed parent in that ripening of the new variety starts about 49 days later than that of 'PE1192W' at July 4$^{th}$, compared to May 16$^{th}$ for 'PE1192W'. Further, fruit of the new variety has lower titratable acidity (TA) and a higher brix:acid ratio than 'PE1192W' at 0.4% TA and a 38 brix:acid ratio for the new variety compared to 1.05% TA and a 10 brix:acid ratio for 'PE1192W'. Additionally, the new variety 'Supech27' has non-showy flowers, compared to showy flowers for 'PE1192W'.

The new variety 'Supech27' can be distinguished from each of the seven unpatented nectarine varieties of the bulk pollen parent: 'PE1391W', 'PE1465W', 'PE1468WF', 'PE1503W', 'PE1505WF', 'PE1525W' and 'PE1541W'. The fruit of the new variety 'Supech27' ripens later than the fruit of each of 'PE1465W', 'PE1468WF', 'PE1503W', 'PE1505WF' and earlier than the fruit of each 'PE1391W', 'PE1525W' and 'PE1541W'. Further, the new variety 'Supech27' has a fruit weight of 235 g, compared to a fruit weight of 219 g for 'PE1391W', a fruit weight of 185 g for 'PE1465W', a fruit weight of 125 g for 'PE1468WF', a fruit weight of 213 g for 'PE1503W', a fruit weight of 204 g for 'PE1505WF', a fruit weight of 203 g for 'PE1525W', and a fruit weight of 300 g for 'PE1541W'.

The new variety 'Supech27' has a Brix:acid of 38 compared to a Brix:acid of 16 for 'PE1391W', 22 for 'PE1465W', 15 for 'PE1468WF', 12 for 'PE1503W', 31 for 'PE1505WF', 30 for 'PE1525W' and 27 for 'PE1541W'. The new variety 'Supech27' has a lower fruit acidity at 0.4 compared to 0.85 for 'PE1391W', 0.64 for 'PE1465W', 0.82 for 'PE1468WF', 1.05 for 'PE1503W', 0.45 for 'PE1505WF', 0.4 for 'PE1525W' and 0.55 for 'PE1541W'.

Additionally, the flowers of the new variety 'Supech27' are non-showy, similar to the flowers of 'PE1465W'. However, they differ from the showy flowers of 'PE1391W', 'PE1468WF', 'PE1503W', 'PE1505WF', 'PE1525W' and 'PE1541W'. Lastly, flowering time for the new variety 'Supech27' starts later than the flowering time of 'PE1391W', 'PE1465W', 'PE1468WF', 'PE1503W', 'PE1505WF', 'PE1525W' and 'PE1541W'.

The new variety 'Supech27' resembles 'Sweet Dream' (U.S. Plant Pat. No. 10,176) in that the fruit of both varieties ripens in the mid-season, and titratable acidity for both are low at 0.4%, however, the new variety has white flesh compared to yellow flesh for the fruit of 'Sweet Dream'. The new variety resembles 'Snow Princess' (U.S. Plant Pat. No. 12,570) in that both varieties ripen in mid-season and have white flesh, but ripening for the new variety starts six days earlier on July 4$^{th}$ compared to July 10$^{th}$ for 'Snow Princess'. Further, overcolor for the new variety covers about the whole surface while overcolor for 'Snow Princess' covers about 80-90% of the surface. The new variety resembles 'Sierra Snow' (U.S. Plant Pat. No. 13,527) in that both varieties have white flesh, but ripening for the new variety begins 28 days later on July 4$^{th}$ compared to June 6$^{th}$ for 'Sierra Snow'.

The new variety 'Supech27' has been shown to maintain its distinguishing characteristics through successive asexual propagations by, for example, cuttings and grafting.

BRIEF DESCRIPTION OF THE DRAWING

The accompanying color photographic illustration taken from a 6-year-old plant shows typical specimens of the foliage and fruit of the present new peach variety 'Supech27'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 3-year-old 'Supech27' trees grown in the vicinity of Wasco, Kern County, Calif., during 2021, and is believed to apply to plants of the variety grown under similar conditions of soil and climate elsewhere.

TREE

General: (Measurements taken on 3-year-old trees unless otherwise noted.).

- *Size*.—Medium. Reaches a height of approximately 3 meters with normal pruning.
- *Vigor*.—Strong. Top shoot growth of about 1.5 meters during the first growing season.
- *Growth*.—Upright-spreading.
- *Type of bearing*.—On one year old shoots.
- *Productivity*.—Very productive. About 850, 25 lb cartons per acre. Thinning and spacing of fruit is necessary.
- *Fertility*.—Self-compatible.
- *Hardiness*.—Hardy in all fruit growing areas of California; winter chilling requirement is approximately 400 hours at or below 7.2° C.
- *Disease resistance/susceptibility*.—No specific testing for relative plant disease resistance/susceptibility has been undertaken. Under close observation in Kern County, Calif., no particular plant/fruit disease resistance/susceptibility has been observed.

Trunk: (Measurements taken at approximately 30 cm above the soil line.).

- *Diameter*.—Approximately 14 cm.
- *Texture*.—Medium shaggy, increases with the age of the tree.
- *Trunk color*.—About Medium Greyed-Green 198B with highlights of Dark Greyed-Orange 166A, becoming darker with age.

Branches: (Measurements taken at approximately 90 cm above the soil line.).

- *Size*.—Approximately 9 cm.
- *Texture*.—Medium shaggy; increasing with tree age.
- *Color*.—About Medium Grey 201B with highlights of Medium Grey-Brown 199B, becoming darker with age.
- *Lenticels density*.—Plentiful, approximately 50 per cm$^2$.
- *Lenticels color*.—About Medium Greyed-Green 197C.
- *Lenticels length*.—Approximately 1-3 mm.
- *Lenticels width*.—Approximately 0.5 mm.

One year old shoots: (Data taken in September at midpoint of current-season growth.).

- *Size*.—Average diameter approximately 6 mm.
- *Type of bearing*.—Even and every year.
- *Color*.—Topside: About Medium Green 137C, becoming Medium Greyed-Orange 165B. Underside: About Medium Green 137C, becoming Medium Greyed-Orange 165B.
- *Internode length*.—Approximately 16 mm, midway in shoot.
- *Lenticels density*.—Medium; about 5 per cm$^2$.
- *Color*.—About Medium Greyed-Green 197C.
- *Lenticel size*.—Very small, difficult to see, approximately 0.2 mm in diameter.
- *Spur length*.—Short, approximately 5 mm.
- *Intensity of anthocyanin coloration on upper side of shoots*.—Medium.

Vegetative buds:

- *Position of vegetative bud in relation to shoot*.—Slightly held out.
- *Bud size*.—Medium, approximately 2.7 mm long by 1.7 mm wide.
- *Bud shape*.—Conical.
- *Bud shape of apex*.—Obtuse.
- *Color*.—About Dark Greyed-Orange 177A.

Flower buds:

- *Bud dimensions*.—Approximately 2 mm long by 1.1 mm wide.
- *Bud shape*.—Ovoid.
- *Color*.—About Dark Greyed-Orange 177B.
- *Ratio of flower buds to vegetative buds*.—2 flower buds:1 vegetative bud.
- *Bud distribution*.—2 buds/node on one year old shoots.

FOLIAGE

Leaves: (Data taken in July on fully expanded leaves at midpoint of current-season growth).

- *Average length*.—Medium; approximately 12.5 cm without petiole.
- *Average width*.—Medium; approximately 3.5 cm.
- *Length*.—Width ratio:Medium; about 3.1:1
- *Time of leaf bud burst*.—Approximately March 1st.

*Shape*.—Lanceolate.
*Color*.—Upper Surface: About Dark Green 139A. Lower Surface: About Dark Green 136B.
*Glossiness of upper side*.—Medium.
*Shape of base*.—Acuminate.
*Angle at apex*.—Acute.
*Venation*.—Pinnately Net Veined.
*Vein color*.—About Light Green 139D with highlights of Medium Greyed-Orange 176C where exposed to sun.
*Presence of red coloration of mid-vein on the lower side*.—Absent or very sparse.
*Surface texture*.—Smooth on both top and bottom surfaces.
*Shape in the cross section*.—Flat.
*Profile*.—Up-folded.
*Leaf blade tip*.—Curved downwardly.
*Density of pubescence for lower side*.—Absent or very sparse.
*Incisions of margin*.—Crenate.

Petiole:
*Average length*.—Medium; approximately 9 mm.
*Average diameter*.—Approximately 2 mm.
*Color*.—About Light Green 139D with highlights of Medium Greyed-Orange 176C where exposed to sun.

Stipules:
*Number/leaf bud*.—Usually 2.
*Typical length*.—Approximately 9 mm.
*Color*.—About Dark Greyed-Orange 166A when dried.
*Persistence*.—Falls off.

Leaf glands:
*Form*.—Globose.
*Average number and arrangement*.—Usually 2-4, alternating. Predominately on petiole.
*Diameter*.—Approximately 0.3 mm.
*Color*.—About Dark Greyed-Yellow 162A, becoming Dark Greyed-Orange 166A over time.

FLOWERS

General:
*Time of beginning of flowering*.—Early for the San Joaquin Valley, Calif.
*Flower blooming period*.—First Bloom: Approximately February 20. Full Bloom: Approximately February 24.
*Location of first bloom*.—At base of tree canopy.
*Location of full bloom*.—Central part of the tree canopy.
*Duration of bloom*.—Approximately 10 days.
*Diameter*.—Medium, approximately 7 mm.
*Form*.—Non-showy.

Pedicels:
*Length*.—Long, approximately 3 mm.
*Diameter*.—Approximately 1.8 mm.
*Color*.—About Medium Green 138B.
*Pubescence*.—Absent.

Sepals:
*Number*.—5.
*Shape*.—Medium ovate.
*Position*.—Adpressed to petals.
*Length*.—Approximately 5 mm.
*Width*.—Approximately 3 mm.
*Surface texture*.—Smooth.
*Color*.—About Dark Greyed-Purple 184A.
*Margin*.—Undulating.
*Frequency of double sepals*.—None.

Petals:
*Number*.—5.
*Arrangement*.—Free.
*Color*.—About Light Pink 54D.
*Surface texture*.—Smooth.
*Length*.—Medium, approximately 12 mm.
*Width*.—Medium, approximately 7 mm.
*Shape*.—Narrow elliptic.
*Apex shape*.—Rounded.
*Base shape*.—Narrows at point of attachment.
*Undulation of margins*.—Medium.
*Frequency of flowers with double petals*.—Never.
*Claw*.—Partially developed.

Stigma:
*Position compared to anthers*.—Above.

Stamens:
*Number*.—About 40.
*Length*.—Variable, ranging from 7 mm to 10 mm.
*Filament color*.—About White 155A with highlights of Light Pink 54D.
*Pollen*.—Present.
*Flower pollen color*.—About Medium Greyed-Orange 166C
*Position compared to petals*.—At the same level.

Anthers:
*Pollen*.—Present.

Pistil:
*Length*.—Approximately 17 mm.
*Ovary diameter*.—Approximately 2 mm.
*Frequency of supplementary pistils*.—Few.
*Stigma position in relation to anthers*.—Above.
*Pubescence*.—Present.

Receptical:
*Depth*.—Medium, about 4 mm.
*Pubescence of inner surface* (*at pink bud stage*).—Absent.
*Pubescence of outer surface*.—Present.

FRUIT

General: (Description taken at firm-mature near Wasco, Kern County, Calif.).
*Time of beginning of fruit ripening*.—Medium, mid-season.
*Date of first pick*.—Approximately July 4.
*Date of last pick*.—Approximately July 15.

Peduncle:
*Length of stem*.—Short, approximately 7 mm.
*Diameter of stem*.—Approximately 3 mm.
*Color of stem*.—About Light Green 139D.

Fruit size:
*Size*.—Very large; about 235 g.
*Height*.—Tall; about 74 mm.
*Diameter perpendicular to suture*.—Broad, approximately 76 mm.
*Diameter ventral side, facing suture*.—Approximately 76 mm.

Fruit shape:
*Shape viewed from apex*.—Circular.
*Shape in lateral view, perpendicular to suture*.—Circular.
*Shape ventral side, facing suture*.—Circular.

*Symmetry viewed from pistil end*.—Symmetric or slightly asymmetric.
*Shape of base*.—Truncate.
*Shape of apex*.—Rounded.
*Depth of stalk cavity*.—Medium; about 8 mm.
*Width of stalk cavity*.—Medium; about 8 mm.
*Depth of suture*.—Absent or very shallow.

Fruit skin:
*Thickness*.—Medium.
*Adherence to flesh*.—Medium.
*Taste*.—Sweet-mild.
*Surface texture*.—Smooth.
*Reticulation*.—Absent.
*Tendency to crack*.—Slight to none.
*Density of pubescence*.—Slight, does not rub up when rubbed.
*Bloom on skin*.—Absent.
*Ground color*.—About Cream-White 155D.
*Relative area of overcolor*. Whole surface.
*Overcolor color of skin*.—About Dark Red 46A
*Pattern of overcolor of skin*.—Solid.
*Number of lenticels*.—None Flesh:
*Ripens*.—Evenly.
*Color*.—About White 155A.
*Texture*.—Crisp-juicy.
*Flavor*.—Sweet, sub-acid about 38 Brix:Acid.
*Firmness*.—Firm; typically 10 lb pressure at harvest.
*Juiceness*.—Medium; able to squeeze free juice easily.
*Sweetness*.—Medium; about 15% brix at harvest.
*Acidity*.—Medium; about 0.40% titratable acidity.
*Adherence to stone*.—Adherent.

Stone:
*Freeness*.—Cling.
*Stone size*.—Medium. Size compared to Fruit: Medium. Length: Approximately 25 mm. Diameter in-line With Suture: Approximately 20 mm. Diameter Perpendicular to Suture Plane: Approximately 23 mm.
*Stone color*.—About Medium Greyed-Yellow 161B when dried.
*Position of maximum*.—Middle.
*Shape in lateral view*.—Circular.
*Shape in ventral view*.—Medium elliptic.
*Shape in basal view*.—Medium elliptic.
*Base shape*.—Nearly straight.
*Apex shape*.—Slight point at tip.
*Ridges*.—Rounded throughout.
*Outgrowing keel*.—Partially developed.
*Ventrical edge*.—Thin with slight wing throughout.
*Dorsal edge*.—Narrow, shallow groove throughout.
*Fibers*.—Not visible.
*Symmetry in lateral view*.—Symmetric or slightly asymmetric.
*Texture of lateral surface*.—Slightly rough.
*Width of stalk end*.—Narrow.
*Tendency to split*.—Rare.

What is claimed is:

1. A new and distinct variety of peach tree named 'Supech27' as herein described.

* * * * *

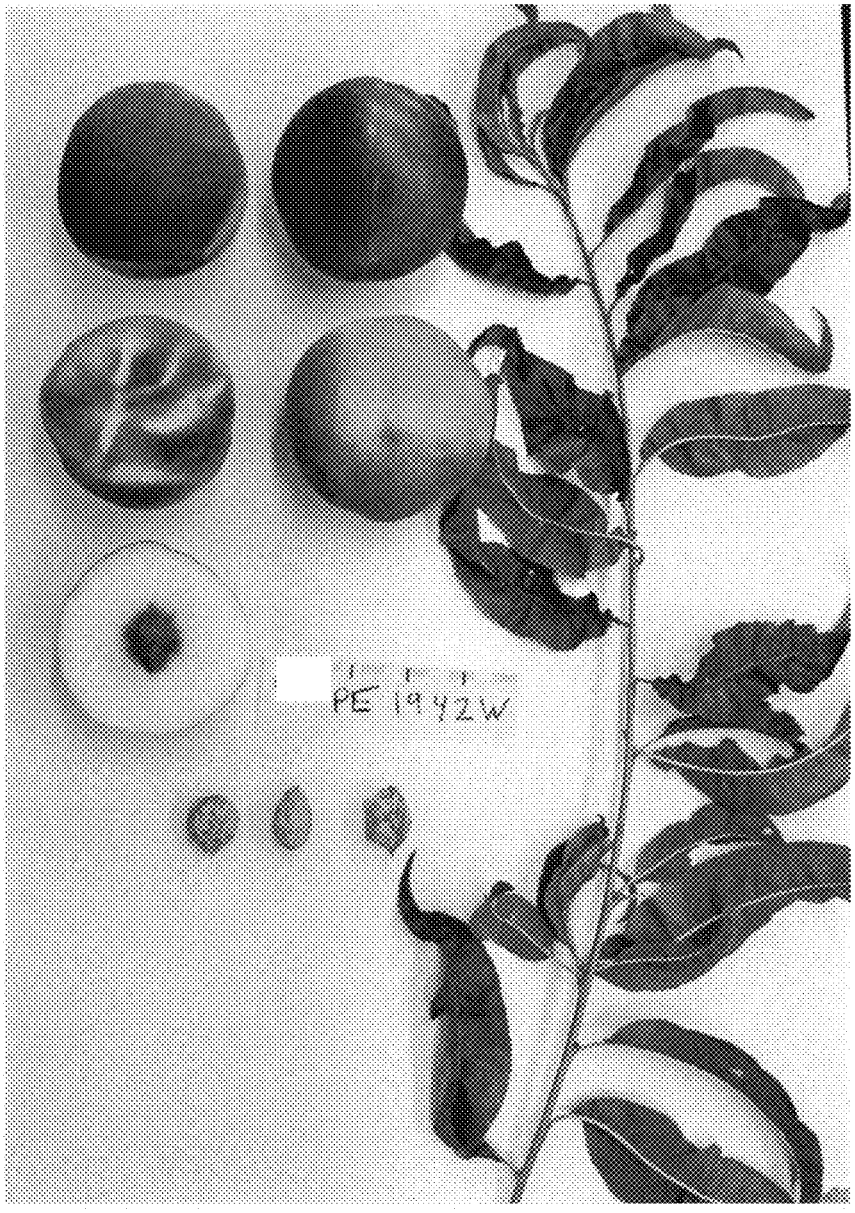
PE 194ZW